United States Patent [19]

Murdock

[11] 4,275,009
[45] Jun. 23, 1981

[54] 1-(AMINOALKYLAMINO)-5,8-DIHYDROXY-4-SUBSTITUTED-ANTHRAQUINONES

[75] Inventor: Keith C. Murdock, Pearl River, N.Y.
[73] Assignee: American Cyanamid Company, Stamford, Conn.
[21] Appl. No.: 43,271
[22] Filed: May 29, 1979
[51] Int. Cl.³ .............................................. C09C 97/26
[52] U.S. Cl. .................................................... 260/380
[58] Field of Search ................................ 260/378, 380
[56] References Cited

U.S. PATENT DOCUMENTS

| | | | |
|---|---|---|---|
| 3,123,605 | 3/1964 | Turetzky et al. | 260/380 |
| 3,281,434 | 10/1966 | Turetzky et al. | 260/380 |
| 3,467,483 | 9/1969 | Bugaut et al. | 260/378 |
| 3,646,072 | 2/1972 | James | 260/380 |
| 3,806,525 | 4/1979 | Kalopissis et al. | 260/380 |
| 3,881,865 | 5/1975 | Greenhalgh et al. | 260/380 |
| 3,992,421 | 11/1976 | Botros | 260/380 |
| 4,138,415 | 2/1979 | Murdock et al. | 260/380 |

FOREIGN PATENT DOCUMENTS 49-22480  2/1974  Japan ..................... 260/380

OTHER PUBLICATIONS

*Anthracene and Anthraquinone*, 1921, pp. 271–272, E. de Barry Barnett, D. Van Nostrand, New York.

*Primary Examiner*—Patrick Garvin
*Assistant Examiner*—Raymond K. Covington
*Attorney, Agent, or Firm*—Edward A. Conroy, Jr.

[57] ABSTRACT

This disclosure describes 1-(aminoalkylamino)-5,8-dihydroxy-4-substituted-anthraquinones useful as chelating agents and for inhibiting the growth of transplanted mouse tumors.

8 Claims, No Drawings

1-(AMINOALKYLAMINO)-5,8-DIHYDROXY-4-SUBSTITUTED-ANTHRAQUINONES

BRIEF SUMMARY OF THE INVENTION

This invention relates to new organic compounds and, more particularly, is concerned with novel 1-(aminoalkylamino)-5,8-dihydroxy-4-substituted-anthraquinones which may be represented by the following general formula:

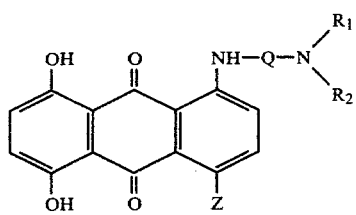

wherein Z is hydroxy or monoalkylamino having from 1 to 3 carbon atoms; Q is a divalent moiety selected from the group consisting of those of the formulae:

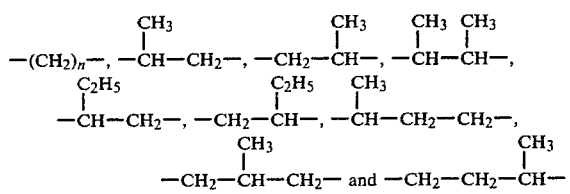

wherein n is an integer from 2 to 4, inclusive; $R_1$ and $R_2$ are each individually selected from the group consisting of hydrogen, alkyl having from 1 to 4 carbon atoms, monohydroxyalkyl having from 2 to 4 carbon atoms and wherein the carbon atom alpha to the nitrogen atom may not bear an hydroxy group, dihydroxyalkyl having from 3 to 6 carbon atoms and wherein the carbon atom alpha to the nitrogen atom may not bear an hydroxy group, formyl, alkanoyl having from 2 to 4 carbon atoms, trifluoroacetyl and moieties of the formulae:

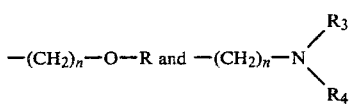

wherein n is an integer from 2 to 4, inclusive, R is alkyl having from 1 to 4 carbon atoms, and $R_3$ and $R_4$ are each individually selected from the group consisting of hydrogen, alkyl having from 1 to 4 carbon atoms, and monohydroxyalkyl having from 2 to 4 carbon atoms and wherein the carbon atom alpha to the nitrogen atom may not bear an hydroxy group, and $R_3$ and $R_4$ taken together with their associated N(itrogen) is morpholino, thiomorpholino, piperazino, 4-methyl-1-piperazino or a moiety of the formula:

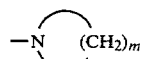

wherein m is an integer from 2 to 6, inclusive; with the proviso that the ratio of the total number of carbon atoms to the sum of the total number of oxygen atoms plus the total number of nitrogen atoms in the side chains at the 1-position and 4-position may not exceed 4. Suitable monohydroxyalkyl and dihydroxyalkyl groups contemplated by the present invention are, for example, β-hydroxyethyl, β-hydroxypropyl, γ-hydroxypropyl, 2,3-dihydroxypropyl, 2,4-dihydroxybutyl, and the like.

A preferred embodiment of the present invention which comprises certain 1-(aminoalkylamino)-4,5,8-trihydroxyanthraquinones may be represented by the following general formula:

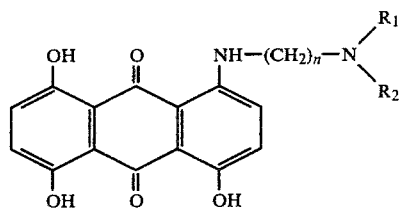

wherein n is an integer from 2 to 4 inclusive, and $R_1$ and $R_2$ are hydrogen, lower alkyl and hydroxylower alkyl.

Also included within the purview of the present invention are the leuco bases and tautomers thereof which may be represented by the following general formulae:

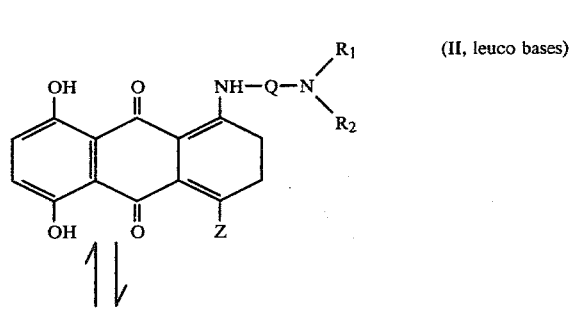

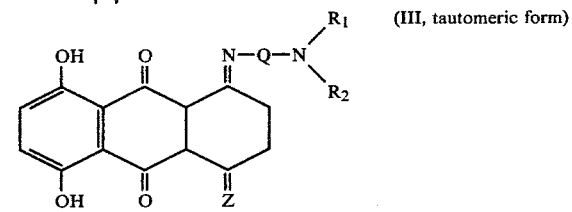

wherein $R_1$, $R_2$ and Q are as hereinabove defined.

DETAILED DESCRIPTION OF THE INVENTION

The novel compounds of the present invention are obtainable as reddish brown to blue crystalline materials having characteristic melting points and absorption spectra and which may be purified by leaching with lower alkanols since many of the free bases are insoluble in water and some of them are insoluble in most organic solvents. The organic bases of this invention (I, II, and III) form nontoxic acid-addition salts with a variety of pharmacologically acceptable organic and inorganic salt-forming reagents. Thus, acid-addition salts, formed by admixture of the organic free base with an acid, suitably in a neutral solvent, are formed with such acids as sulfuric, phosphoric, hydrochloric, hydrobromic, sulfamic, citric, lactic, malic, succinic, tartaric, acetic, benzoic, gluconic, ascorbic, and the like. For purposes of this invention the free bases are equivalent to their non-toxic acid-addition salts. The acid-addition salts of the organic bases of the present invention are, in general, crystalline solids, relatively soluble in water, methanol and ethanol but relatively insoluble in non-polar organic solvents such as diethyl ether, benzene, toluene, and the like.

The novel compounds of the present invention may be readily prepared in accordance with the following reaction scheme:

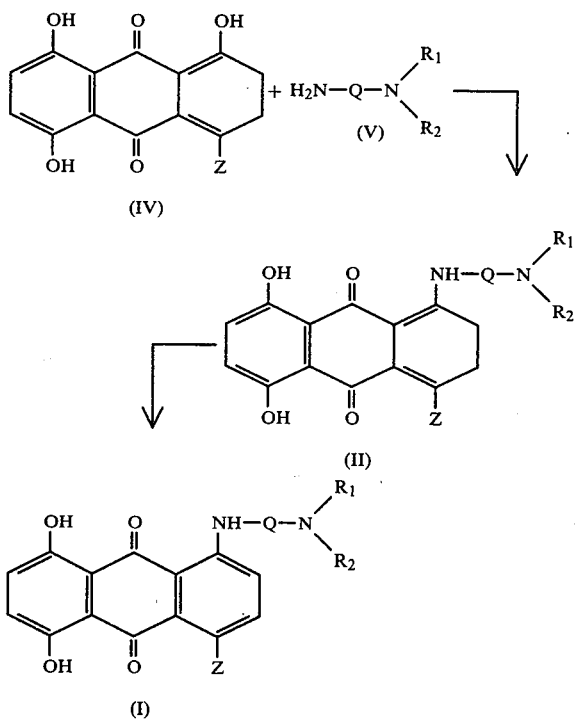

wherein $R_1$, $R_2$, Z and Q are as hereinabove defined. In accordance with this reaction scheme, leuco 1,4,5,8-tetrahydroxyanthraquinone or leuco 1-monoalkylamino-4,5,8-trihydroxyanthraquinone (IV) is condensed with an appropriate alkylene diamine (V) in a solvent such as N,N,N',N'-tetramethylethylenediamine, methanol, ethanol, water, dimethylformamide, or mixtures thereof at from about 40° C. to about 60° C. under an atmosphere of nitrogen for several hours to produce the corresponding leuco bases (II). The leuco bases (II) may be readily oxidized to the fully aromatic derivatives (I) by a variety of methods such as air oxidation or treatment with hot nitrobenzene, or treatment with chloranil, hydrogen peroxide, or sodium perborate.

Alternatively the novel compounds of the present invention may be prepared in accordance with the following reaction scheme:

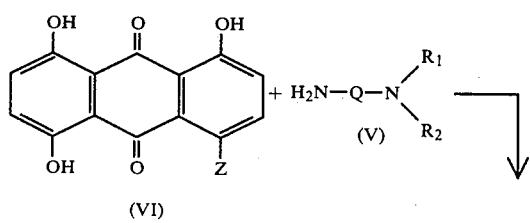

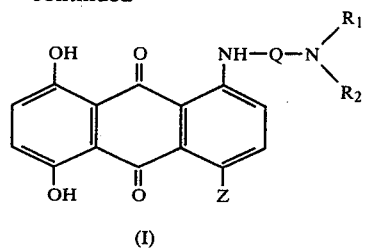

wherein $R_1$, $R_2$, Z and Q are as hereinabove defined. In accordance with this reaction scheme, 1,4,5,8-tetrahydroxy-9,10-anthracenedione or 1-monoalkylamino-4,5,8-trihydroxy-9,10-anthracenedione (VI) is condensed with an appropriate alkylene diamine (V) in a solvent such as N,N,N',N'-tetramethylethylenediamine, 2-methoxyethanol, or N,N-dimethylformamide and the like at the reflux temperature for 1–20 hours to produce the corresponding bases.

The novel compounds described herein are useful as chelating, complexing or sequestering agents. The complexes formed with polyvalent metal ions are particularly stable and usually soluble in various organic solvents. These properties, of course, render them useful for a variety of purposes wherein metal ion contamination presents a problem; e.g., as stabilizers in various organic systems such as saturated and unsaturated lubricating oils and hydrocarbons, fatty acids and waxes, wherein transition metal ion contamination accelerates oxidative deterioration and color formation. They are further useful in analyses of polyvalent metal ions which may be complexed or extracted by these materials and as metal carriers. Other uses common to sequestering agents are also apparent for these compounds. In addition, the leuco bases (II) are useful as intermediates in the preparation of the fully aromatic derivatives (I).

The novel compounds of the present invention also possess the property of inhibiting the growth of transplanted mouse tumors as established by the following tests.

LYMPHOCYTIC LEUKEMIA P388 TEST

The animals used are DBA/2 mice all of one sex, weighing a minimum of 17 g. and all within a 3 gram weight range. There are 5 or 6 animals per test group. The tumor transplant is by intraperitoneal injection of 0.1 ml. of dilute ascitic fluid containing $10^6$ cells of lymphocytic leukemia P388. The test compounds are administered intraperitoneally on days one, 5 and 9 (relative to tumor inoculation) at various doses. The animals are weighed and survivors are recorded on a regular basis for 30 days. The median survival time and the ratio of survival time for treated (T)/control (C) animals are calculated. The positive control compound is 5-fluorouracil given as a 60 mg./kg. injection. The results of this test with representative compounds of the present invention appear in Table I. The criterion for efficacy is $T/C \times 100 \geq 125\%$.

TABLE I

| | Lymphocytic Leukemia P388 Test | | |
|---|---|---|---|
| Compound | Dose (mg./kg.) | Median Survival Time (Days) | T/C × 100 (Percent) |
| 1-[(2-Dimethyl- | 50 | 17.0 | 170 |
| aminoethyl)- | 25 | 16.0 | 160 |
| amino]-4,5,8- | 12.5 | 14.0 | 140 |

TABLE I-continued

| | Lymphocytic Leukemia P388 Test | | |
|---|---|---|---|
| Compound | Dose (mg./kg.) | Median Survival Time (Days) | T/C × 100 (Percent) |
| trihydroxyanthraquinone | | | |
| Control | 0 | 10.0 | — |
| 5-Fluorouracil | 60 | 15.0 | 150 |
| 1-[[2-(2-Hydroxyethylamino)ethyl]amino]-4,5,8-trihydroxyanthraquinone | 25 | 23.5 | 235 |
| | 12.5 | 19.5 | 195 |
| | 6.25 | 19.5 | 195 |
| | 3.12 | 19.0 | 190 |
| | 1.56 | 17.0 | 170 |
| | 0.78 | 15.5 | 155 |
| Control | 0 | 10.0 | — |
| 5-Fluorouracil | 60 | 19.0 | 190 |
| 1-[(2-Dimethylaminoethyl)-amino]-4-ethylamino-5,8-dihydroxyanthraquinone | 100 | 15 | 150 |
| | 50 | 14 | 140 |
| | 25 | 13 | 130 |
| Control | 0 | 10 | — |
| 5-Fluorouracil | 20 | 16 | 160 |

MELANOTIC MELANOMA B16

The animals used are C57BC/6 mice, all of the same sex, weighing a minimum of 17 g. and all within a 3 g. weight range. There are normally 10 animals per test group. A one-gram portion of melanotic melanoma B16 tumor is homogenized in 10 ml. of cold balanced salt solution and a 0.5 ml. aliquot of the homogenate is implanted intraperitoneally into each of the test mice. The test compounds are administered intraperitoneally on days one through 9 (relative to tumor inoculation) at various doses. The animals are weighed and survivors are recorded on a regular basis for 60 days. The median survival time and the ratio of survival time for treated (T)/control (C) animals are calculated. The positive control compound is 5-fluorouracil given as a 20 mg./kg. injection. The results of this test with representative compounds of the present invention appear in Table II. The criterion for efficacy is T/C×100≧125%.

TABLE II

| | Melanotic Melanoma B16 Test | | |
|---|---|---|---|
| Compound | Dose (mg./kg.) | Median Survival Time (Days) | T/C × 100 (Percent) |
| 1-[(2-Dimethylaminoethyl)-amino]-4,5,8-trihydroxyanthraquinone | 25 | 31.5 | 185 |
| | 12.5 | 35.2 | 209 |
| | 6.2 | 28.5 | 168 |
| Control | 0 | 17.0 | — |
| 5-Fluorouracil | 20 | 30.0 | 176 |
| 1-[[2-(2-Hydroxyethylamino)ethyl]amino]-4,5,8-trihydroxyanthraquinone | 10 | >31 | >145 |
| | 5 | 28.5 | 129 |
| | 2.5 | 29.5 | 134 |
| | 1.2 | 28.5 | 129 |
| Control | 0 | 22 | — |
| 5-Fluorouracil | 20 | 28.5 | 129 |

Also embraced within the purview of the present invention are therapeutic compositions of matter useful for ameliorating cancer diseases in mammals and containing certain 1-(aminoalkylamino)-4,5,8-trihydroxyanthraquinones (or the leuco bases and non-toxic acid-addition salts thereof) which may be represented by the following structural formula:

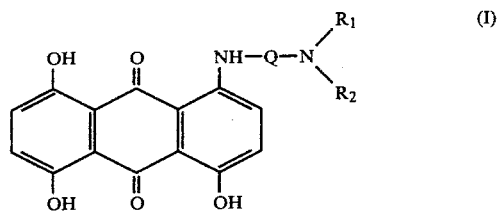

wherein $R_1$ is hydrogen or alkyl having from 1 to 4 carbon atoms, $R_2$ is hydrogen or alkyl having from 1 to 4 carbon atoms, $R_1$ and $R_2$ taken together with their associated N(itrogen) is as hereinbefore defined for $R_3$ and $R_4$ taken together with their associated N(itrogen), and Q is as hereinbefore defined. This aspect of the invention includes the novel compositions of matter and the method of inducing the regression and/or palliation of leukemia and related cancers in mammals therewith.

The active ingredients of the therapeutic compositions and the novel compounds of the present invention inhibit transplanted mouse tumor growth and induce regression and/or palliation of leukemia and related cancers in mammals when administered in amounts ranging from about 1 mg. to about 0.4 g. per kilogram of body weight per day. A preferred dosage regimen for optimum results would be from about 1.0 mg. to about 50 mg. per kilogram of body weight per day, and such dosage units are employed that a total of from about 70 mg. to about 3.5 g. of the active compound for a subject of about 70 kg. of body weight are administered in a 24 hour period. This dosage regimen may be adjusted to provide the optimum therapeutic response. For example, several divided doses may be administered daily or the dose may be proportionally reduced as indicated by the exigencies of the therapeutic situation. A decided practical advantage is that the active compound may be administered in any convenient manner such as by the oral, intravenous, intramuscular, or subcutaneous routes.

The active compounds may be orally administered, for example, with an inert diluent or with an assimilable edible carrier, or they may be enclosed in hard or soft shell gelatin capsules, or they may be compressed into tablets, or they may be incorporated directly with the food of the diet. For oral therapeutic administration, the active compounds may be incorporated with excipients and used in the form of ingestible tablets, buccal tablets, troches, capsules, elixirs, suspensions, syrups, wafers, and the like. Such compositions and preparations should contain at least 0.1% of active compound. The percentage of the compositions and preparations may, of course, be varied and may conveniently be between about 2 to about 60% of the weight of the unit. The amount of active compound in such therapeutically useful compositions is such that a suitable dosage will be obtained. Preferred compositions or preparations according to the present invention are prepared so that an oral dosage unit form contains between about 1 and 400 milligrams of active compound.

The tablets, troches, pills, capsules and the like may also contain the following: A binder such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, lactose or saccharin may be added or a flavoring agent such as peppermint, oil of wintergreen, or cherry flavoring. When the dosage unit form is a capsule, it may contain, in addition to materials of the above type, a liquid carrier. Various other materials may be present as coatings or to otherwise modify the physical form of the dosage unit. For instance, tablets, pills, or capsules may be coated with shellac, sugar or both. A syrup or elixir may contain the active compound, sucrose as a sweetening agent, methyl and propylparabens as preservatives, a dye and flavoring such as cherry or orange flavor. Of course, any material used in preparing any dosage unit form should be pharmaceutically pure and substantially non-toxic in the amounts employed. In addition, the active compounds may be incorporated into sustained-release preparations and formulations.

The active compounds may also be administered parenterally or intraperitoneally. Solutions of the active compound as a free base or pharmacologically acceptable salt can be prepared in water suitably mixed with a surfactant such as hydroxypropylcellulose. Dispersions can also be prepared in glycerol, liquid polyethylene glycols, and mixtures thereof and in oils. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases the form must be sterile and must be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), suitable mixtures thereof, and vegetable oils. The proper fluidity can be maintained, for example, by the use of a coating such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like. In many cases it will be preferable to include isotonic agents, for example sugars or sodium chloride. Prolonged absorption of the injectable compositions can be brought about by the use in the compositions of agents delaying absorption, for example aluminum monostearate and gelatin.

Sterile injectable solutions are prepared by incorporating the active compound in the required amount in the appropriate solvent with various of the other ingredients enumerated above, as required, followed by filtered sterilization. Generally, dispersions are prepared by incorporating the various sterilized active inredient into a sterile vehicle which contains the basic dispersion medium and the required other ingredients from those enumerated above. In the case of sterile powders for the preparation of sterile injectable solutions, the preferred methods of preparation are vacuum drying and the freeze-drying technique which yield a powder of the active ingredient plus any additional desired ingredient from a previously sterile-filtered solution thereof.

As used herein, "pharmaceutically acceptable carrier" includes any and all solvents, dispersion media, coatings, antibacterial and antifungal agents, isotonic and absorption delaying agents and the like. The use of such media and agents for pharmaceutical active substances is well known in the art. Except insofar as any conventional media or agent is incompatable with the active ingredient, its use in the therapeutic compositions is contemplated. Supplementary active ingredients can also be incorporated into the compositions.

It is especially advantageous to formulate parenteral compositions in dosage unit form for ease of administration and uniformity of dosage. Dosage unit form as used herein refers to physically discrete units suited as unitary dosages for the mammalian subjects to be treated; each unit containing a predetermined quantity of active material calculated to produce the desired therapeutic effect in association with the required pharmaceutical carrier. The specification for the novel dosage unit forms of the invention are dictated by and directly dependent on (a) the unique characteristics of the active material and the particular therapeutic effect to be achieved, and (b) the limitations inherent in the art of compounding such an active material for the treatment of disease in living subjects having a diseased condition in which bodily health is impaired as herein disclosed in detail.

The principal active ingredient is compounded for convenient and effective administration in effective amounts with a suitable pharmaceutically-acceptable carrier in dosage unit form as hereinbefore disclosed. A unit dosage form can, for example, contain the principal active compound in amounts ranging from about 0.1 to about 500 mg., with from about 10 to about 500 mg. being preferred. Expressed in proportions, the active compound is generally present in from about 10 to about 500 mg./ml. of carrier. In the case of compositions containing supplementary active ingredients, the dosages are determined by reference to the uyual dose and manner of administration of the said ingredients.

Regression and palliation of cancers are attained, for example, using intraperitoneal administration. A single intravenous dosage or repeated daily dosages can be administered. Daily dosages up to about 5 or 10 days are often sufficient. It is also possible to dispense one daily dosage or one dose on alternate or less frequent days. As can be seen from the dosage regimens, the amount of principal active ingredient administered is a sufficient amount to aid regression and palliation of the leukemia or the like, in the absence of excessive deleterious side effects of a cytotoxic nature to the hosts harboring the cancer. As used herein, cancer disease means blood malignancies such as leukemia, as well as other solid and non-solid malignancies such as the melanocarcinomas, lung carcinomas, and mammary tumors. By regression and palliation is meant arresting or retarding the growth of the tumor or other manifestation of the disease compared to the course of the disease in the absence of treatment.

This invention will be described in greater detail in conjunction with the following specific examples.

EXAMPLE 1

1-[(2-Dimethylaminoethyl)amino]-4,5,8-trihydroxyanthraquinone

A reaction mixture comprising 52.9 g. of N,N-dimethylethylenediamine, 300 ml. of N,N,N',N'-tetramethylethylenediamine and 54.8 g. of leuco-1,4,5,8-tetrahydroxyanthraquinone is flushed with nitrogen and stirred under nitrogen for 2 hours while heating with an oil bath kept at 49°-51° C. The mixture is allowed to cool under nitrogen, then is filtered. The material on the filter is washed with ethanol. The filtrate and washings are combined and air is bubbled into the solution for 10 hours while the temperature of the solution is maintained at 23° C. The solvent is evaporated to give a slightly gummy, blue-black solid. The solid is mostly dissolved in 300 ml. of chloroform-methanol (6:1). This solution, containing some insoluble material, is chromatographed by high pressure liquid chromatography on 1.4 kg. of silica gel, eluting with chloroform-methanol (6:1). The eluate cuts are monitored by thin layer chromatography on silica gel using chloroform-methanol (6:1). The fractions giving only the chromatographically faster of two purple spots are combined and evaporated in vacuo to provide 3.4 g. of the product of the Example as an almost black solid, mp. 171°-172° C.

EXAMPLE 2

1-[(2-Dimethylaminopropyl)amino]-4,5,8-trihydroxyanthraquinone

The use of $N^2$, $N^2$-dimethyl-1,2-propanediamine rather than N,N-dimethylethylenediamine in the procedure of Example 1 affords the title compound.

EXAMPLE 3

1-[(4-Aminobutyl)amino]-4,5,8-trihydroxyanthraquinone

Repetition of the method of Example 1 using 1,4-diaminobutane instead of N,N-dimethylethylenediamine gives the desired product.

EXAMPLE 4

Leuco-1-[[2-(1-pyrrolidinyl)ethyl]amino]-4,5,8-trihydroxyanthraquinone

The method of Example 1 is repeated using N-2-pyrrolidinoethylamine in place of N,N-dimethylethylenediamine and omitting the oxidation with air to give the product as a dark, red-brown solid.

EXAMPLE 5

1-[[2-(2-Hydroxyethylamino)ethyl]amino]-4,5,8-trihydroxyanthraquinone

A suspension of 5.44 g. of 1,4,5,8-tetrahydroxy-9,10-anthracenedione [P. G. Marshall, J.C.S., 254 (1937)] in a solution of 2.08 g. of 2-(2-aminoethylamino)ethanol in 50 ml. of N,N,N',N'-tetramethylethylenediamine is stirred and heated under reflux for 17 hours, then allowed to cool. The solid is collected by filtration and washed 3 times with N,N,N',N'-tetramethylethylenediamine, then twice with hexane. The first filtrate and the diamine washings are combined and the solution is allowed to stand for 60 hours as a solid separates. This solid is collected and washed as above to give 0.524 g. of a dark blue solid. This solid is purified by dry column chromatography on deactivated (i.e., air-equilibrated) silica gel by the procedure of B. Loev and M. M. Goodman [Chem. and Ind., 2026 (1967)], eluting with chloroform-methanol (3:1) and monitoring the eluate fractions by thin layer chromatography on silica gel with the same solvent mixture. The cuts which showed only the slower of two purple spots were pooled and evaporated to give 0.42 g. of the product of the Example as a dark blue solid, mp. 196°-198° C.

EXAMPLE 6

1-[[2-(2-Methylaminoethylamino)ethyl]amino]-4,5,8-trihydroxyanthraquinone

The procedure of Example 5 is repeated using N-(2-methylaminoethyl)ethylenediamine in place of 2-(2-aminoethylamino)ethanol, giving the title compound as a purple-black solid.

EXAMPLE 7

1-[(3-Dimethylaminopropyl)amino]-4-ethylamino-5,8-dihydroxyanthraquinone

A mixture of 2.74 g. of leuco-1,4,5,8-tetrahydroxyanthraquinone, 0.45 g. of ethylamine, a trace of sodium hydrosulfite and 60 ml. of aqueous methanol is stirred and warmed to 50° C. for one hour. To this is added 1.1 g. of dimethylaminopropylamine and the mixture is stirred and warmed at 50°-60° C. for 2 hours. Air is bubbled through this mixture while heating on a steambath for 6 hours. The mixture is cooled and the title product is collected.

We claim:

1. A compound selected from the group consisting of those of the formula:

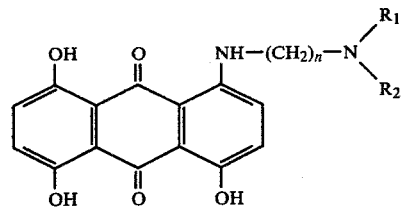

wherein n is an integer from 2 to 4, inclusive; $R_1$ and $R_2$ are each individually selected from the group consisting of hydrogen, alkyl having from 1 to 4 carbon atoms and monohydroxyalkyl having from 2 to 4 carbon atoms and wherein the carbon atom alpha to the nitrogen atom may not bear an hydroxy group; with the proviso that the ratio of the total number of carbon atoms to the sum of the total number of oxygen atoms plus the total number of nitrogen atoms in the side chains at the 1-position may not exceed 4; and the pharmacologically acceptable acid-addition salts thereof.

2. A compound selected from the group consisting of those of the formula:

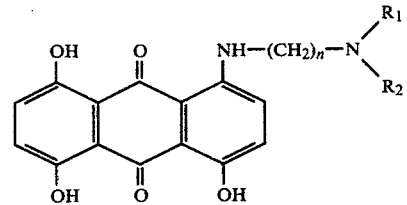

wherein n is an integer from 2 to 4, inclusive; $R_1$ and $R_2$ are each individually selected from the group consisting of hydrogen, alkyl having from 1 to 4 carbon atoms and monohydroxyalkyl having from 2 to 4 carbon atoms and wherein the carbon atom alpha to the nitrogen atom may not bear an hydroxy group; with the proviso that the ratio of the total number of carbon atoms to the sum of the total number of oxygen atoms plus the total number of nitrogen atoms in the side chains at the 1-position may may not exceed 4; and the pharmacologically acceptable acid-addition salts thereof.

3. 1-[(2-dimethylaminoethyl)amino]-4,5,8-trihydroxyanthraquinone.

4. 1-[(2-dimethylaminopropyl)amino]-4,5,8-trihydroxyanthraquinone.

5. 1-[(4-aminobutyl)amino]-4,5,8-trihydroxyanthraquinone.

6. Leuco-1-[[2-(-pyrrolidinyl)ethyl]amino]-4,5,8-trihydroxyanthraquinone.

7. 1-[[2-(2-hydroxyethylamino)ethyl]amino]-4,5,8-trihydroxyanthraquinone.

8. 1-[2-(2-methylaminoethylamino)ethylamino]-4,5,8-trihydroxyanthraquinone.

* * * * *